United States Patent [19]

Brownlee et al.

[11] 3,949,759

[45] Apr. 13, 1976

[54] CARDIAC PACING APPARATUS

[75] Inventors: Robert R. Brownlee, State College; G. Frank O. Tyers, Hershey, both of Pa.

[73] Assignee: Research Corporation, New York, N.Y.

[22] Filed: May 5, 1975

[21] Appl. No.: 574,385

[52] U.S. Cl............................ 128/419 PG; 128/422
[51] Int. Cl.² ........................................... A61N 1/36
[58] Field of Search ...... 128/419 PG, 421, 422, 423

[56] References Cited
UNITED STATES PATENTS

| | | | |
|---|---|---|---|
| 3,253,596 | 5/1966 | Keller, Jr. | 128/419 PG |
| 3,433,228 | 3/1969 | Keller, Jr. | 128/419 PG |
| 3,651,799 | 3/1972 | Daynard | 128/419 PG |
| 3,669,120 | 6/1973 | Nielsen | 128/419 PG |
| 3,783,878 | 1/1974 | Thaler et al. | 128/419 PG |
| 3,870,050 | 3/1975 | Greatbatch | 128/419 PG |

OTHER PUBLICATIONS

Fischler et al., "IEEE Transactions On Bio-Medical Electronics," Vol. BME-16, No. 1, Jan. 1969, pp. 64–68.

Primary Examiner—William E. Kamm
Attorney, Agent, or Firm—Cooper, Dunham, Clark, Griffin & Moran

[57] ABSTRACT

A cardiac pacing apparatus includes a trigger pulse generator which generates trigger pulses at a predetermined minimum rate when the natural heart rate fails to exceed the predetermined minimum rate and which follows the natural heart rate when the heart rate is above the predetermined rate, an output pulse generator for generating artificial heart stimulating pulses, a timing interval generator for generating a fixed timing interval in response to the generation of each artificial heart stimulating pulse, and an inhibit gate for selectively applying only those trigger pulses which occur outside the fixed timing intervals to the output pulse generator. The output pulse generator is maximum-rate limited as an inverse function of the fixed timing interval duration regardless of the input rate, and pulses at the minimum predetermined rate, as established by the trigger pulse generator, are generated after an escapement interval in the absence of natural cardiac activity. The trigger pulse generator may be a triggerable astable multivibrator and the timing interval generator may be a nonretriggerable monostable multivibrator.

7 Claims, 3 Drawing Figures

CARDIAC PACING APPARATUS

BACKGROUND OF THE INVENTION

This invention relates to cardiac pacers and relates more particularly to an improved synchronous ventricular programmed pacer.

Existing cardiac pacers are generally of two basic types. The first type, designated fixed rate pacers, provides a constant rate output independent of biologic cardiac activity. This type of pacer is simple, and therefore quite reliable, but can be unsafe if normal cardiac activity returns unexpectedly. In an attempt to overcome this problem, a second variety of more complex R wave programmed pacers has been developed. These units attempt to overcome the principal disadvantage inherent in fixed rate pacers by providing means to monitor heart activity and control pacer output as a function thereof to prevent competition between pacer stimuli and normal cardiac activity.

Prior art programmed pacers, also referred to as adaptive or triggered pacers, can be divided into two basic categories. The first category is the demand pacer, in which the generation of artificial cardiac stimuli is inhibited during normal heart function. Pacers in this category are also referred to as inhibited or suppressed type units. The second category of programmed pacers, referred to as R wave synchronous, triggered or standby pacers, are not inhibited during normal heart function but, rather, emit pulses synchronized with normal heart activity. In the absence of normal heart activity, both categories supply stimuli at a predetermined fixed rate, usually in the order of 70 pulses per minute.

Each of the two known categories of programmed pacers have certain inherent deficiencies. Demand pacers are designed to deliver fixed rate pacing pulses whenever the natural heart rate falls below a predetermined minimum. This type of unit is therefore designed to shut itself off whenever the sensed heart rate is above the predetermined rate. Accordingly, a detected interference signal occurring at normal heart signature rate will completely inhibit the operation of a demand pacer, resulting in complete loss of pacer function. Interfering signals at pulse rates below normal heart rates can also be a serious problem in this type of unit since these rates, when combined with the low physiologic rate encountered in heart block, can also cause complete loss of pacer function. Attempts to filter or otherwise attenuate interference signals have not been fully successful.

Synchronous R wave pacers are designed to overcome this problem by permitting output pulses to occur in synchronism with sensed heart rates during normal cardiac activity rather than being inhibited by such activity as are demand pacers. Should the normal heart rate fall below a predetermined minimum rate, for example 70 pulses per minute, the synchronous pacer delivers pacing pulses at a fixed, predetermined rate that overrides the lower physiologic activity rate. Accordingly, synchronous pacers are not inhibited by external interference fields at biologic rates, as are demand pacers.

In overcoming the interference problem, however, conventional synchronous pacers introduce a second serious problem. In the conventional synchronous pacer, it is necessary to incorporate an input inhibit period, referred to as the refractory delay period, during which the synchronous pacer is blind to input activity from the heart as well as from interference sources. The purpose of this refractory delay period is to prevent the synchronous pacer from triggering on interference signals at higher than biologic rates. Thus, each time the synchronous pacer delivers an output pulse to the heart, the unit becomes insensitive to either a noise input pulse or a premature ventricular contraction (PVC) occuring during the input refractory delay period. While it is desirable to thus make the unit insensitive to noise pulses during the refractory period, the inability to recognize a PVC may result in the discharge of a competitive artificial stimulus during the vulnerable period which follows the PVC. This condition has the potential for inducing fibrillation.

One prior art solution to this latter problem is to reduce the input refractory delay period to minimize the period of insensitivity to PVCs. However, this solution leads to other disadvantages in the presence of relatively high rate interference fields. Since the output rate of the synchronous pacer in noise fields is limited only by the duration of the input refractory delay period, as this period is shortened to improve recognition of PVCs, the maximum output rate of the unit in higher frequency noise fields can increase beyond the maximum permissible pacing rate. Thus, a conflict exists between the necessity for minimizing the refractory period to minimize the possibility of not detecting PVCs and the necessity for increasing the refractory period in order to ensure a safe maximum rate in noise fields. In conventional synchronous pacers, a typical compromise value for the input refractory delay period is about 400 milliseconds, which allows a maximum rate of about 150 pulses per minute in the presence of interference at or above this rate. This compromise is far from ideal, since a heart rate of 150 beats per minute can decompensate elderly patients, or those with cardiac or vascular disorders. Furthermore, the 400 millisecond refractory delay still permits some early PVCs to remain unsensed, so that the possibility of competitive pacing is not eliminated.

Representative prior art demand pacers are shown in U.S. Pat. Nos. 3,661,157, 3,678,937 and 3,693,626. These units are all subject to being inhibited in the presence of external interference at rates which mock normal biologic heart rates. A prior art synchronous pacemaker is shown in U.S. Pat. No. 3,433,228. This unit, in common with other prior art synchronous pacers, cannot sense premature ventricular contractions that fall within its own refractory delay period, and is also capable of being triggered at relatively high rates by interference. A complex dual channel pacer is disclosed in Fischler et al *Atrial Synchronized Demand Heart Pacing*, IEEE Transactions on Biomedical Engineering, Vol. BME-16, No. 1, January 1969. The disclosed system is based on both synchronized and demand pacemaker concepts, but is nevertheless subject to being completely inhibited in the presence of interference fields in the range of normal heart rates.

SUMMARY OF THE INVENTION

An object of the invention is to provide a cardiac pacing apparatus which cannot be completely inhibited in the presence of any interference or noise field.

It is a further object of the invention to provide a cardiac pacer that will always be sensitive to premature ventricular contractions as well as interference inputs, so as to minimize the possibility of competitive pacing.

Still another object is to provide a cardiac pacer in which the output pulse rate is limited to a safe maximum rate regardless of the rate of biologic or interference input signals.

To these and other ends, one embodiment of the present invention contemplates a sensing and pacing electrode at the cardiac site for detecting natural heart stimulating pulses as well as for coupling artificial heart generating pulses to the heart. Detected cardiac contraction signals are amplified and fed to a trigger pulse generator which is triggered at the natural heart rate when the heart rate is above a fixed, predetermined rate, and which free-runs at the predetermined rate in absence of a natural pulse rate above this rate. The trigger pulse generator output is coupled to an output pulse generator through an inhibit gate, which in its normal, enabled state permits trigger pulses to be coupled to the output pulse generator. The output pulse generator is coupled to the input of a timing interval generator, which serves to generate a fixed timing interval each time the output pulse generator generates an artificial heart stimulating pulse. When an artifical heart stimulating pulse is generated, the timing interval generator is triggered and its output causes the inhibit gate to be opened for the fixed timing interval. The output pulse generator is thus prevented from being retriggered for the fixed timing interval regardless of the nature of biologic or interference inputs to the trigger pulse generator during the fixed timing interval.

Since the trigger pulse generator is sensitive to input signals, and the output pulse generator is only inhibited after it has generated an output pulse, and then only for a fixed interval, it is impossible to completely inhibit the unit in the presence of interference. Furthermore, since the trigger pulse generator is always responsive to input pulses, the likelihood of competitive pacing resulting from an unsensed, premature ventricular contraction is minimized. Finally, as the unit is not rendered insensitive to premature ventricular contractions during the inhibit interval, this interval can be optimized in order to precisely control the maximum output rate of the output pulse generator without increasing the danger of competitive pacing.

DETAILED DESCRIPTION

Figure 1:
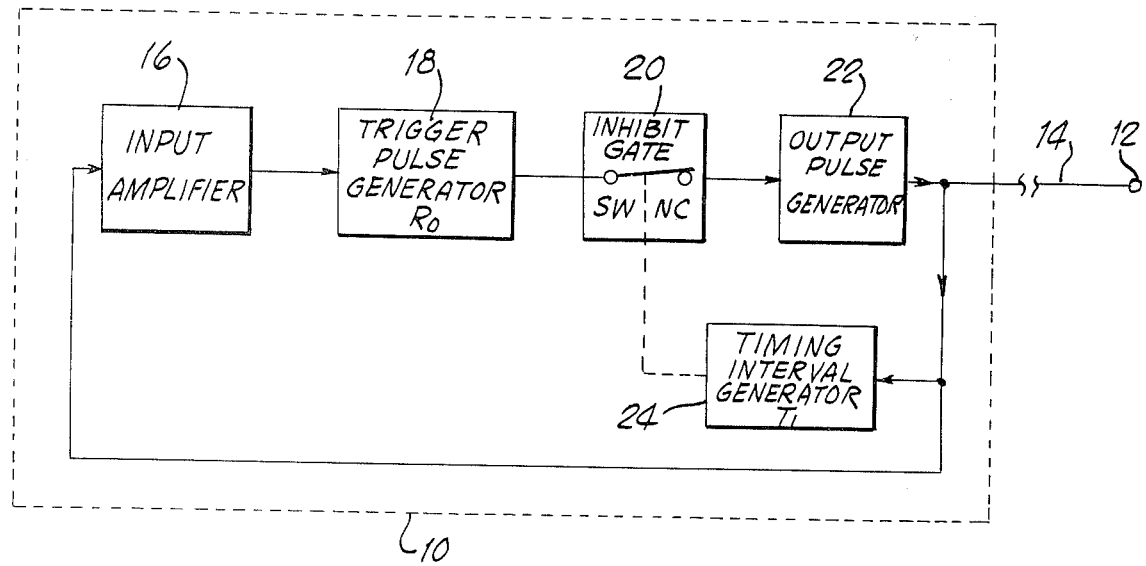
FIG. 1 is a system block diagram of a cardiac pacing apparatus in accordance with the invention.

Referring to FIG. 1 of the drawings, there is shown in simplified block form a cardiac pacing apparatus generally identified by reference numeral 10. A conventional sensing and pacing electrode 12 is suitably positioned at the cardiac site and is connected to pacer 10 by a lead 14. The single electrode 12 is used in conjunction with an appropriate return, for both sensing and pacing, in a manner well known to those skilled in the art.

Natural cardiac activity is sensed by electrode 12 and is fed to an input amplifier 16 by lead 14. Cardiac signals are amplified and processed in amplifier 16 and are then fed to trigger pulse generator 18. In the absence of cardiac activity above a fixed predetermined minimum rate Ro from input amplifier 16, trigger pulse generator 18 will act as a free-running pulse generator and will generate trigger pulses at the predetermined minimum rate Ro, typically about 70 pulses per minute. However, in the presence of input pulses above the predetermined rate, which may represent natural heart activity or interference, the pulse generator is externally triggered at the higher input rate. After the occurrence of an input trigger pulse to trigger pulse generator 18, no output pulse from this generator in the free-running mode can occur until after an escape interval, which is typically the interval between pulses in the free-running mode. In this manner, the danger of competitive pacing during the vulnerable period following a PVC input is minimized. Thus, the output of pulse generator 18 is a pulse train at the rate of normal cardiac activity (or interference) when the normal cardiac rate (or interference rate) is above the predetermined rate Ro, and reverts after an escape interval to a pulse train at the rate Ro upon removal of a natural or interference pulse rate above the predetermined rate. When the natural heart rate falls below the predetermined rate and pulse generator 18 reverts to its fixed rate free-running mode, artificial heart stimulating pulses are generated at the predetermined rate, as discussed in greater detail below, and the heart is biologically inhibited from responding to natural stimulating pulses below the predetermined rate.

The output of trigger pulse generator 18 is fed to an inhibit gate 20, which is normally enabled and is accordingly symbolically represented by a normally-closed series switch SW in FIG. 1. Trigger pulses from generator 18 will normally be coupled through inhibit gate 20 to an output pulse generator 22. The output of pulse generator 22 is coupled to the heart in a conventional manner by lead 14 and sensing and pacing electrode 12, which operates in conjunction with a conventional return.

Output pulse generator 22 is also coupled to a timing interval generator 24 which provides a control signal to inhibit gate 20. Each time output pulse generator 22 generates an artificial heart stimulating pulse, timing interval generator 24 is triggered, and a fixed timing interval control signal of duration T1 is applied to inhibit gate 20. This timing signal causes gate 20 to be disabled for the fixed timing interval T1, symbolically represented by an opening of switch SW in FIG. 1, to thereby inhibit the coupling of trigger pulses from trigger pulse generator 18 to output pulse generator 22. Each time an artificial heart stimulating pulse is generated, output pulse generator 22 is thus inhibited from generating a subsequent output pulse for the fixed timing interval T1.

After the period T1, when timing interval generator 24 has timed out, inhibit gate 20 will again be enabled, and the output of trigger pulse generator 18 will again be coupled to output pulse generator 22. Accordingly, output pulse generator 22 is maximum-rate limited as an inverse function of the fixed timing interval T1. Significantly, while the output pulse generator is rendered insensitive to trigger pulses during this inhibit interval, trigger pulse generator 18 is always receptive to input pulses, such as PVCs, and generator 18 will be triggered and reset by such pulses. Since a new escape interval is initiated for each PVC, no output pulse will be delivered during the vulnerable time following the PVC, since the escape interval is of greater duration than the vulnerable time.

In the absence of noise or arrhythmias related to premature ventricular contractions, the apparatus of FIG. 1 operates in a manner which is essentially similar to that of the conventional synchronous pacer. In the absence of a natural pulse rate at or above the predetermined minimum rate Ro, trigger pulse generator 18 continuously generates trigger pulses at the predetermined rate. Fixed timing interval T1 of timing interval generator 24 is selected to be an appropriate interval of shorter duration than the interval between trigger pulses at the rate Ro, so that when timing interval generator 24 is triggered by output pulse generator 22, timing interval T1 terminates before the next sequential trigger pulse is generated. Inhibit gate 20 is accordingly always in its enabled (normally-closed) state at the occurrence of each free-running trigger pulse output from generator 18, and output pulse generator 22 is continuously triggered at the predetermined minimum rate Ro of generator 18. Illustratively, the predetermined rate Ro of trigger pulse generator 18 may be set to a rate of about 70 pulses per minute, which would result in an interval between trigger pulses of about 850 milliseconds. Fixed timing interval T1 of timing interval generator 24 might then be set to provide an inhibit pulse duration of approximately 600 milliseconds, which corresponds to a predetermined maximum allowable output rate of about 100 pulses per minute regardless of the rate of biologic or interference inputs. The duration of fixed timing interval T1, which is analogous to the refractory delay period in conventional synchronous pacers, is thus substantially increased from the typical refractory period of about 400 milliseconds, which corresponds to a less desirable maximum allowable pulse rate of about 150 pulses per minute. This increased duration, and the resulting decrease in the predetermined maximum pacing rate, are made possible because the interval T1 need no longer be reduced to a compromise value to prevent competitive pacing in the presence of premature ventricular contractions, as in conventional synchronous pacers.

When the natural heart rate exceeds the predetermined rate Ro, trigger pulse generator 18 will be triggered synchronously with biological cardiac activity in a manner similar to that of conventional synchronous pacers. If the natural biological input rate should exceed the maximum rate permitted by timing interval generator 24, output pulse generator 22 will provide artificial noncompetitive pulses at an output rate which is an integral division of the input rate. For example, if T1 is chosen to limit the output rate to 100 pulses per minute, and a biologic input of 120 pulses per minute is received, then the output rate will be 60 pulses per minute. Thus, in the absence of an interference input, the pacer of FIG. 1 will generate artificial noncompetitive synchronous pulses at a minimum rate determined by the parameter Ro (typically about 70 pulses per minute) up to a maximum rate determined by the parameter T1 (typically 100 pulses per minute), no matter how fast or slow the biologic cardiac input. In the presence of interference fields, the maximum output pulse rate is similarly limited by the parameter T1 of timing interval generator 24.

For interference rates below the free-running rate Ro of trigger pulse generator 18, the absolute minimum output pulse rate will correspond to a time interval equal to the sum of the interval T1 of timing interval generator 24 and the escape interval, the latter being typically but not necessarily the same as the interval between successive pulses of trigger pulse generator 18 when this generator is operating in a free-running mode. Thus for the representative values of about 600 millisecond for T1 and about 850 milliseconds spacing between trigger pulses as an escape interval, which corresponds to a free-running rate Ro of 70 pulses per minute, output pulses will be generated once every 1,450 milliseconds, which corresponds to a minimum rate of just over 40 pulses per minute. However, this rate of just over 40 pulses per minute. However, this rate represents the absolute worst-case performance in noise fields, and will occur only for an interference input at a pulse rate of just over 40 pulses per minute. For interference at pulse rates lower than this worst-case value, the average rate of output pulse generator 22 will be above the worst-case rate, with the output rate approaching Ro as the interference pulse rate approaches zero. It should be emphasized that the worst-case minimum output rate occurs only at one particular interference pulse rate, and only when there is concurrently a complete heart block. Thus, the range of pacer output rates over the entire spectrum of interference input rates is benign, with the single possible exception of the one dip to the worst-case minimum rate, which occurs only at a single interference input rate and only during heart block. It would also be possible to raise the minimum rate by modifying the parameters Ro and T1. For example, a free-running trigger pulse rate Ro of 80 pulses per minute with a corresponding escape interval of 750 milliseconds and a fixed timing interval T1 of about 450 milliseconds (corresponding to a maximum rate of about 130 pulses per minute) will result in an absolute minimum output pulse rate of about 50 pulses per minute. Clearly, when compared to either the possibility of complete inhibition in noise fields as in the demand pacer, or the problems of competitive pacing and high rate pacing that can occur with the conventional synchronous pacer, the configuration disclosed herein represents a substantial improvement in overall performance. It should also be recognized that this configuration may additionally incorporate a short input refractory circuit as conventionally employed ahead of the triggerable pulse generator, for the purpose of avoiding multiple triggering on complex biologic waveforms or avoidance of T wave recognition.

Figure 2:
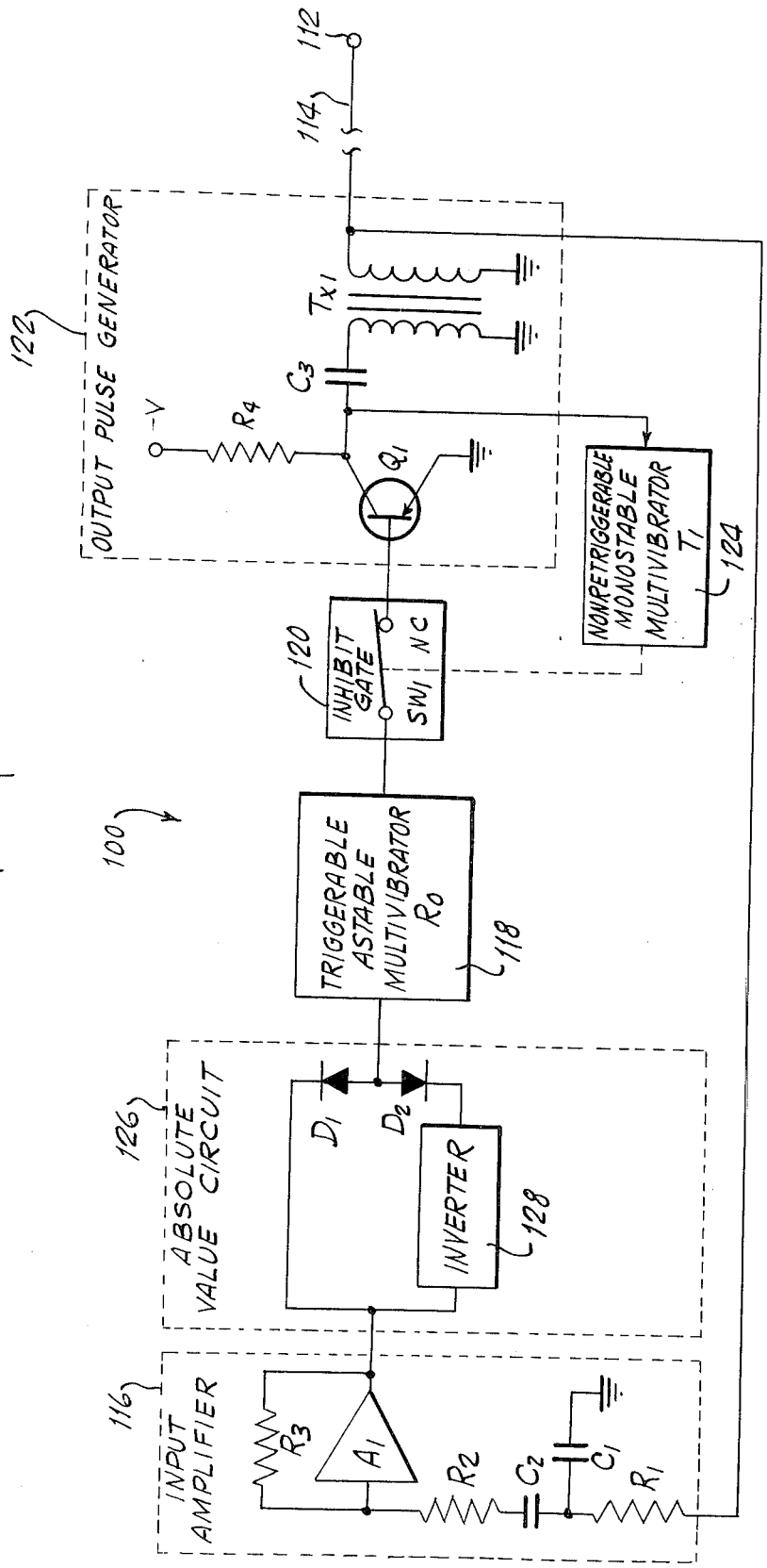
FIG. 2 is a detailed block diagram of the pacing apparatus of FIG. 1.

Referring now to FIG. 2 of the drawings, there is shown a more detailed block diagram of the cardiac pacing apparatus of FIG. 1. As in FIG. 1, a conventional sensing and pacing electrode 112 is connected to a pacing apparatus 100 by a lead 114. Functional blocks 116 through 124 in FIG. 2 correspond to more particular embodiments of blocks 16 through 24 of FIG. 1.

Input amplifier 116 is shown as a bandpass amplifier comprising an amplifier A1 in combination with an input filter and feedback network composed of resistors R1, R2 and R3, and capacitors C1 and C2. The purpose of the input filter is to restrict input bandwidth and thereby reduce sensitivity to interference outside the range of frequencies of interest.

The output of amplifier 116 is fed to an absolute value circuit 126, which comprises an inverter 128 and diodes D1 and D2. This circuit permits the pacer to be triggered on either positive or negative potentials. A negative output from input amplifier 116 will be coupled directly to a triggerable astable multivibrator 118 through diode D1, while a positive output from input amplifier 116 will be inverted by inverter 128 and then coupled to astable 118 through diode D2. Thus, for either positive or negative outputs from input amplifier 116, astable 118 will receive a negative polarity triggering pulse.

The triggerable pulse generator function indicated by block 18 in FIG. 1 and discussed above is implemented by triggerable astable multivibrator 118. In the absence of an input from absolute value circuit 126, astable 118 free-runs at its fixed predetermined rate R$o$. In the presence of a natural heart rate or an interference rate above the predetermined rate, astable 118 will shift to a triggerable mode, and will generate output pulses at the input rate.

The output of triggerable astable 118 is coupled to an output pulse generator 122 through an inhibit gate 120. Inhibit gate 120 serves as a normally-closed switching means and is therefore functionally represented by a normally-closed switch SW1 in FIG. 2. In its normally-closed, or enabled, state this switch couples the output of triggerable astable multivibrator 118 to output pulse generator 122, which generates an artificial heart stimulating pulse for each trigger pulse received.

Output pulse generator 122 is shown in simplified form in FIG. 2 by transistor Q1, collector resistor R4 connected to a source of negative potential, coupling capacitor C3 and output coupling transformer Tx1. The output from transistor Q1 is coupled to nonretriggerable monostable multivibrator 124, which serves to generate a fixed timing interval T1 each time it is triggered by an output pulse from transistor Q1 of output pulse generator 122. Each time monostable 124 is triggered, it generates a control output of duration T1, which is coupled to inhibit gate 120 and causes normally-closed switch SW1 to open for the interval T1. Thus, after each output pulse generated by transistor Q1, output pulse generator 122 is effectively disconnected from triggerable astable multivibrator 118, and the application of trigger pulses to the output pulse generator is thereby inhibited. At the end of each timing interval T1, monostable multivibrator 124 returns to its quiescent state and switch SW1 responsively returns to its normally-closed state, thus again enabling the transmission of trigger pulses from astable 118 to output pulse generator 122.

Figure 3:
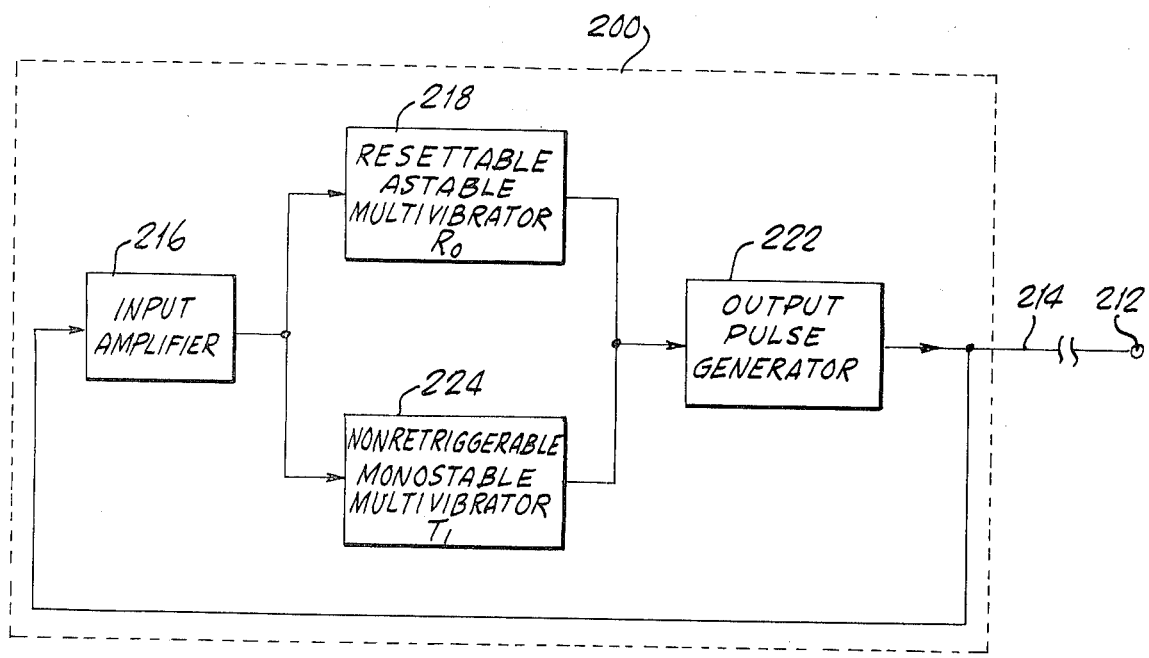
FIG. 3 is a system block diagram of a cardiac pacing apparatus showing an alternate embodiment of the invention.

An alternate embodiment of the invention is shown in the system block diagram of FIG. 3. A cardiac pacing apparatus 200 has a sensing and pacing electrode 212 which is connected to the pacer by means of a lead 214, as discussed above in connection with FIG. 1 and FIG. 2. Similarly, input amplifier 216 and output pulse generator 222 correspond to input amplifiers 16 and 116 and output pulse generators 22 and 122 of FIG. 1 and FIG. 2, respectively. In the embodiment of FIG. 3, however, the triggering and inhibiting functions are accomplished by a resettable (rather than triggerable) astable multivibrator 218 in conjunction with a nonretriggerable monostable multivibrator 224. Astable 218 and monostable 224 are both directly triggered by input amplifier 216, and the output of each multivibrator provides an input to output pulse generator 222.

The performance of the configuration shown in FIG. 3 is similar to that of the previously discussed embodiment, and therefore will not be discussed in detail. Briefly, in the absence of biologic or noise inputs, artificial stimulating pulses are generated by output pulse generator 222 at a predetermined rate R$o$, with an escape interval typically corresponding to 1/R$o$, as determined by the free-running rate of astable 218. In the presence of a detected natural or artificial stimulating pulse rate greater than R$o$, the maximum output rate of output pulse generator 222 is controlled by the timing interval T1 of monostable 224. The absolute minimum output pulse rate is a function of parameters R$o$ and T1, as discussed above.

Essentially, the embodiment of FIG. 3 is a parallel rather than serial combination of pulse generating and pulse inhibiting functions. The triggerable astable multivibrator 118 of FIG. 2 has been replaced by resettable astable multivibrator 218, which is triggered in parallel with nonretriggerable monostable multivibrator 224. While both triggerable astable 118 of FIG. 2 and resettable astable 218 of FIG. 3 free-run at the rate R$o$ in the absence of an input signal, resettable astable 218 is reset without generating an output each time it is triggered. Thus, in the presence of any input signal at a rate greater than R$o$, resettable astable 218 generates no output. However, nonretriggerable monostable multivibrator 224, which is also directly triggered by input amplifier 216, will receive an input. Thus, each time an input pulse is received from amplifier 216, monostable 224 will receive an input and astable 218 will be reset.

Each time monostable 224 is triggered by an input pulse from amplifier 216, it will generate a fixed timing interval pulse of duration T1. The leading edge of this pulse will trigger output pulse generator 222, and since monostable 224 is nonretriggerable, and resettable astable 218 cannot be fired by an input pulse, output pulse, output pulse generator 222 will be prevented from receiving a subsequent trigger pulse for an interval T1 each time monostable 224 is fired, in similar fashion to the configuration previously discussed in connection with FIG. 1 and FIG. 2. Accordingly, the parallel configuration of FIG. 3 is functionally equivalent to the serial embodiment of FIG. 1 and FIG. 2 with reference to performance in noise fields. Finally, since astable multivibrator 218 is reset and begins a new escape interval on every detected natural heart pulse, competitive pacing with premature ventricular contractions is unlikely, as in the series configuration.

We claim:

1. A cardiac pacing apparatus, which comprises:
   triggerable means for generating artificial heart stimulating pulses;
   means for detecting natural heart stimulating pulses and said artificial heart stimulating pulses and producing a signal in accordance therewith;
   control means responsive to said signal from said detecting means for generating trigger pulses to normally trigger said triggerable pulse generating means at a rate between the limits of a predetermined minimum rate and a predetermined maximum rate, said control means generating trigger pulses in direct response to said signal from said detecting means at said predetermined minimum rate in the absence of a detected natural heart stimulating pulse rate above said minimum rate, said control means generating trigger pulses in direct response to said signal from said detecting means at the detected natural heart rate when the natural rate is greater than said minimum rate but less than said maximum rate, and said control means generating trigger pulses at no higher than said predetermined maximum rate when the natural pulse rate equals or exceeds said maximum rate.

2. An apparatus as in claim 1, wherein said control means for generating trigger pulses to trigger said triggerable pulse generating means comprises:
- a triggerable astable multivibrator directly responsive to said signal from said detecting means for generating trigger pulses at said predetermined minimum rate in the absence of a detected natural heart pulse rate above said minimum rate and for generating trigger pulses at the detected natural heart rate when the natural rate is greater than said minimum rate; and
- a nonretriggerable monostable multivibrator responsive to the output of said means for generating artificial heart stimulating pulses, for generating a fixed timing interval output proportional to said predetermined maximum rate, said output controlling the application of trigger pulses from said triggerable astable multivibrator to said triggerable means for generating artificial heart stimulating pulses to limit the output rate of said triggerable means to no greater than said predetermined maximum rate when the natural pulse rate equals or exceeds said maximum rate.

3. An apparatus as in claim 1, wherein said control means for generating trigger pulses to trigger said triggerable pulse generating means comprises:
- a resettable astable multivibrator directly responsive to said signal from said detecting means for generating trigger pulses at said predetermined minimum rate in the absence of a detected natural heart pulse rate above said minimum rate; and
- a nonretriggerable monostable multivibrator directly responsive to the signal from said detecting means for generating trigger pulses at the detected natural heart rate when the natural rate is greater than said minimum rate and less than said maximum rate, and for generating a fixed timing interval proportionaal to said predetermined maximum rate to limit the trigger pulse output rate of said monostable multivibrator to said predetermined maximum rate when the natural pulse rate equals or exceeds said maximum rate.

4. A cardiac pacing apparatus, which comprises:
- means for detecting natural heart stimulating pulses and producing a signal in accordance therewith;
- means directly responsive to said signal from said detecting means for generating a train of trigger pulses and for providing a predetermined free-running minimum trigger pulse output rate, the rate of said trigger pulses being determined by the detected rate of the natural heart stimulating pulses when said natural pulse rate is above said minimum predetermined rate, and the trigger pulse rate reverting to the predetermined minimum rate when the detected natural pulse rate drops below said predetermined minimum rate;
- triggerable means for generating artificial heart stimulating pulses;
- means for generating a fixed timing interval in response to the generation of each of said artificial heart stimulating pulses; and
- means responsive to said fixed timing interval generating means for selectively applying only those trigger pulses which occur outside the fixed timing intervals to said means for generating artificial heart stimulating pulses, to trigger the generation of artificial heart stimulating pulses which are maximum-rate limited as an inverse function of the fixed timing interval duration.

5. An apparatus as in claim 4, wherein the means for generating a train of trigger pulses comprises a triggerable astable multivibrator, the means for generating a fixed timing interval comprises a nonretriggerable monostable multivibrator, and the means for selectively applying trigger pulses to said means for generating artificial heart stimulating pulses comprises normally-closed switching means connected between said triggerable astable multivibrator and said artificial heart stimulating pulse generator, for normally applying said trigger pulses to said generating means, said switching means being opened for each fixed timing interval generated by said nontriggerable monostable multivibrator to inhibit the application of trigger pulses to said pulse generator for each said fixed timing interval.

6. A cardiac pacing apparatus which comprises:
- triggerable means for generating artificial heart stimulating pulses;
- means for detecting natural heart stimulating pulses and said artificial heart stimulating pulses and producing a signal in accordance therewith;
- first means directly responsive to said signal from said detecting means for triggering said artificial heart stimulating pulse generating means at a predetermined free-running minimum rate in the absence of a detected natural or artificial stimulating pulse rate greater than said predetermined rate; and
- second means directly responsive to said detecting means for triggering said artificial heart stimulating pulse generating means at the detected rate in the presence of a detected natural or artificial stimulating pulse rate greater than said predetermined rate, and for preventing the retriggering of said artificial pulse generating means for a predetermined interval upon each triggering of said artificial heart stimulating pulse generating means, to cause said artificial pulse generating means to be triggered no faster than a maximum rate which is an inverse function of said predetermined interval.

7. A cardiac pacing apparatus as in claim 6, wherein said first means for triggering said artificial heart stimulating pulse generating means at a predetermined rate comprises a resettable astable multivibrator, and said second means for triggering said artificial heart stimulating pulse generating means comprises a nonretriggerable monostable multivibrator.

* * * * *

UNITED STATES PATENT AND TRADEMARK OFFICE
CERTIFICATE OF CORRECTION

PATENT NO. : 3,949,759
DATED : April 13, 1976
INVENTOR(S) : Robert R. Brownlee and G. Frank O. Tyers It is certified that error appears in the above-identified patent and that said Letters Patent are hereby corrected as shown below:

Column 1, line 41, change "rate" to --rates--

Column 4, line 4, change "R$o$" to --Ro--
          line 19, change "R$o$" to --Ro--

Column 5, line 11, change "R$o$" to --Ro--
          line 19, change "R$o$" to --Ro--
          line 20, change "R$o$" to --Ro--
          line 42, change "R$o$" to --Ro--
          line 56, change "R$o$" to --Ro--

Column 6, line 6, change "R$o$" to --Ro--
          line 10, delete entire line
          line 17, change "R$o$" to --Ro--
          line 27, change "R$o$" to --Ro--
          line 28, change "R$o$" to --Ro--

Column 7, line 9, change "R$o$" to --Ro--
          line 66, change "R$o$" to --Ro--
          line 67, change "R$o$" to --Ro--

Column 8, line 2, change "R$o$" to --Ro--
          line 14, change "R$o$" to --Ro--

Column 9, line 36, change "tionaal" to --tional--

Signed and Sealed this

Thirteenth Day of July 1976

[SEAL]

Attest:

RUTH C. MASON
*Attesting Officer*

C. MARSHALL DANN
*Commissioner of Patents and Trademarks*